US008851268B2

(12) United States Patent
Kameda

(10) Patent No.: US 8,851,268 B2
(45) Date of Patent: Oct. 7, 2014

(54) APPARATUS AND METHOD OF MANUFACTURING ABSORBENT ARTICLE

(75) Inventor: Noritomo Kameda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 616 days.

(21) Appl. No.: 13/201,024

(22) PCT Filed: Feb. 23, 2010

(86) PCT No.: PCT/JP2010/052736
§ 371 (c)(1),
(2), (4) Date: Oct. 31, 2011

(87) PCT Pub. No.: WO2010/101045
PCT Pub. Date: Sep. 10, 2010

(65) Prior Publication Data
US 2012/0037474 A1    Feb. 16, 2012

(30) Foreign Application Priority Data

Mar. 2, 2009   (JP) .................................. 2009-048393

(51) Int. Cl.
*B61F 13/00* (2006.01)
*A61F 13/15* (2006.01)

(52) U.S. Cl.
CPC ..... *A61F 13/15772* (2013.01); *A61F 13/15731* (2013.01)
USPC .................. 198/502.3; 198/464.1; 198/339.1

(58) Field of Classification Search
USPC ......... 156/64, 378, 516, 556; 198/339.1, 340, 198/395, 464.1, 502.3
See application file for complete search history.

(56) References Cited

U.S. PATENT DOCUMENTS

| 5,045,135 A | 9/1991 | Meissner |
| 5,359,525 A | 10/1994 | Weyenberg |

(Continued)

FOREIGN PATENT DOCUMENTS

| JP | 02-228962 A | 9/1990 |
| JP | 04-314443 A | 11/1992 |

(Continued)

OTHER PUBLICATIONS

Office Action issued on Dec. 28, 2012 by the Chinese Patent Office in corresponding Chinese Application No. 2010-80010500.3, English translation.

(Continued)

*Primary Examiner* — Mark A Deuble
(74) *Attorney, Agent, or Firm* — Lowe Hauptman & Ham LLP

(57) ABSTRACT

An apparatus for manufacturing an absorbent article includes a processing device that, processes semi-finished products, and an inspecting device that inspects whether an actual processing position by the processing device is within an allowable range of the process target position on the semi-finished product. The inspecting device includes, a sensor section located in the transport direction and outputting a detection signal while the actual processing position of the semi-finished product is being detected, a reference signal outputting section outputting a reference signal having a waveform in which one wavelength is equivalent to a unit transport amount corresponding to a single semi-finished product, the reference signal having a first waveform portion at a phase corresponding to the allowable range in the wavelength, and a determining section determining whether the actual processing position is within the allowable range by comparing the detection signal with the reference signal.

6 Claims, 8 Drawing Sheets

(56) References Cited

U.S. PATENT DOCUMENTS

| | | | |
|---|---|---|---|
| 6,224,699 B1 | 5/2001 | Bett et al. | |
| 6,408,917 B1 | 6/2002 | Bett et al. | |
| 6,652,686 B1 * | 11/2003 | Coenen et al. | 156/64 |
| 6,986,820 B2 * | 1/2006 | Coenen et al. | 156/64 |
| 2006/0196594 A1 * | 9/2006 | Shimizu et al. | 156/64 |
| 2010/0181007 A1 * | 7/2010 | Yamamoto | 156/64 |

FOREIGN PATENT DOCUMENTS

| | | |
|---|---|---|
| JP | 2002-530130 A | 9/2002 |
| JP | 2005-315651 A | 11/2005 |
| JP | 2005315651 A | 11/2005 |
| JP | 2008-154964 A | 7/2008 |
| JP | 2008154964 A | 7/2008 |

OTHER PUBLICATIONS

Office Action mailed Sep. 12, 2013, corresponds to Chinese patent application No. 201080010500.3.

International Search Report for PCT/JP2010/052736 mailed May 25, 2010.

* cited by examiner

APPARATUS AND METHOD OF MANUFACTURING ABSORBENT ARTICLE

RELATED APPLICATIONS

The present application is a National Phase of International Application Number PCT/JP2010/052736, filed Feb. 23, 2010 and claims priority from, Japanese Application Number 2009-048393, filed Mar. 2, 2009.

TECHNICAL FIELD

The present invention relates to an apparatus and method of manufacturing an absorbent article such a disposable diaper and a sanitary napkin.

BACKGROUND ART

Absorbent articles such as disposable diapers are manufactured by performing a process such as embossing and heat-seal processing to a plurality of semi-finished products transported in an aligned manner in a transporting direction in its production line. In order to reject poorly processed semi-finished products, an inspection is performed during the transportation of the semi-finished products.

As an illustrative example of such an inspection method, PTL 1 discloses a method using an infrared camera. That is to say, an image of a temperature distribution in a semi-finished product is acquired by imaging each semi-finished product, which is being transported, with an infrared camera, an actual processing position is specified on the basis of a contour position of the semi-finished product by processing the image by a process such as binarization, and it is determined whether or not the specified processing position is within an allowable range of a regular process target position determined by the contour position.

CITATION LIST

Patent Literature

PTL 1: JP-A 2002-530130

DISCLOSURE OF INVENTION

Problems to be Solved by the Invention

However, an infrared camera is generally expensive. Also, since an actual processing position is specified by a thermal distribution showing heat generated in the processing etc., in order to carry out imaging while the temperature of the portion that has been actually processed is still high, the infrared camera needs to be provided directly after each processing section. As a result, these cameras are high in cost and thus results in an increased production cost. That is to say, an inspection method using infrared cameras cannot be applied to a production line that produces cost-sensitive products concentrated on basic parts.

The present invention has been made in view of such a problem and its object is to reduce the production cost when manufacturing an absorbent article by processing a semi-finished product and inspecting whether or not the actual processing position is within an allowable range of a process target position.

Means for Solving the Problems

In order to achieve the object described above, the main aspect of the present invention is:

an apparatus for manufacturing an absorbent article, including:

a processing device that, while a plurality of semi-finished products of the absorbent article is being transported in an aligned manner in a transport direction, processes the semi-finished product; and an inspecting device that, while the plurality of semi-finished products of the absorbent article is being transported in the aligned manner in the transport direction, inspects whether or not an actual processing position by the processing device is within an allowable range of the process target position on the semi-finished product, wherein, the inspecting device includes, a sensor section that is located at a predetermined position in the transport direction and that outputs a detection signal while the actual processing position of the semi-finished product is being detected, a reference signal outputting section that outputs a reference signal having a waveform in which one wavelength is equivalent to a unit transport amount corresponding to a single semi-finished product, the reference signal having a first waveform portion at a phase corresponding to the allowable range in the wavelength, and a determining section that determines whether or not the actual processing position is within the allowable range by comparing the detection signal with the reference signal.

Further, a method of manufacturing an absorbent article, that, while a plurality of semi-finished products of the absorbent article is being transported in an aligned manner in a transport direction, processes the semi-finished product, and that inspects whether or not an actual processing position is within an allowable range of the process target position on the semi-finished product, includes:

detecting the actual processing position of the semi-finished product at a predetermined position in the transport direction and outputting a detection signal while the actual processing position of the semi-finished product is being detected;

outputting a reference signal having a waveform in which one wavelength is equivalent to a unit transport amount corresponding to a single semi-finished product, the reference signal having a first waveform portion at a phase corresponding to the allowable range in the wavelength; and determining whether or not the actual processing position is within the allowable range by comparing the detection signal with the reference signal.

Other aspects of the present invention shall be elucidated in the specification with reference to accompanying drawings.

Advantageous Effects of the Invention

According to an aspect of the invention, it is possible to reduce the production cost when manufacturing an absorbent article by processing a semi-finished product and inspecting whether or not the actual processing position is within an allowable range of a process target position.

MODE FOR CARRYING OUT THE INVENTION

Figure 1A:
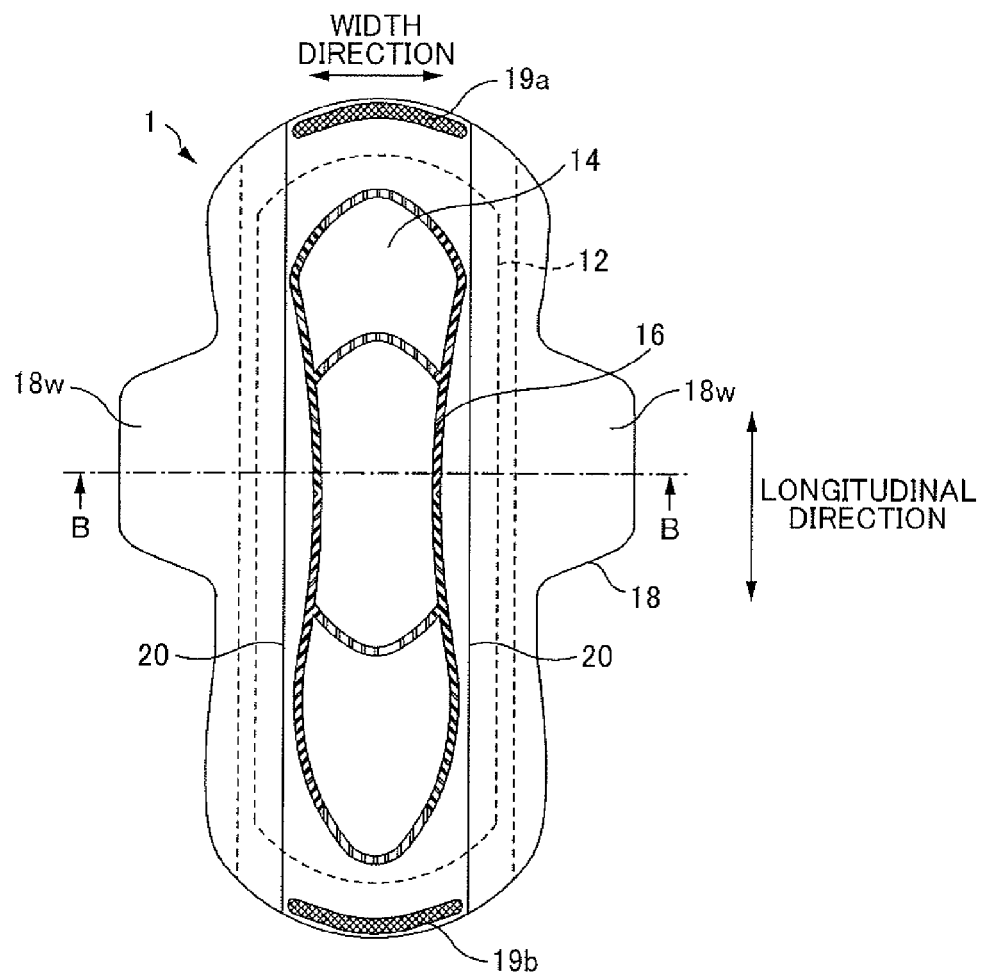
FIG. 1A is a plan view of a front side of a sanitary napkin 1.

At least the following matters will be disclosed in the present specification and accompanying drawings.

First, an apparatus for manufacturing an absorbent article, includes:

a processing device that, while a plurality of semi-finished products of the absorbent article is being transported in an aligned manner in a transport direction, processes the semi-finished product; and an inspecting device that, while the plurality of semi-finished products of the absorbent article is being transported in the aligned manner in the transport direction, inspects whether or not an actual processing position by the processing device is within an allowable range of the process target position on the semi-finished product, wherein, the inspecting device includes, a sensor section that is located at a predetermined position in the transport direction and that outputs a detection signal while the actual processing position of the semi-finished product is being detected, a reference signal outputting section that outputs a reference signal having a waveform in which one wavelength is equivalent to a unit transport amount corresponding to a single semi-finished product, the reference signal having a first waveform portion at a phase corresponding to the allowable range in the wavelength, and a determining section that determines whether or not the actual processing position is within the allowable range by comparing the detection signal with the reference signal.

With such an apparatus for manufacturing the absorbent article, a pass/fail determination of the actual processing position can be performed with a simple structure including the sensor section, the reference signal outputting section and the determining section. Accordingly, the apparatus for manufacturing the absorbent article can be made at a low cost without using expensive inspection equipment such as an infrared camera and the investment burden can be reduced. As a result, the production cost of the absorbent article can be reduced.

Further, in addition to the reference signal, since the detection signal will also be outputted in accordance with the transport amount, an inspection can be performed at a high accuracy even if there is a change in the transport speed of the semi-finished product.

It is preferable that, in the apparatus for manufacturing an absorbent article as described above, a transport operation of the plurality of semi-finished products in the transport direction is performed by a transport mechanism;

the reference signal outputting section has an input shaft to which a rotational operation synchronized with the transport operation of the transport mechanism is inputted, the reference signal outputting section being capable of setting the first waveform portion to correspond to a predetermined phase of an angle of rotation of the input shaft; and for the unit transport amount, an amount of rotation that is an integer multiple (an integer being greater than or equal to one) of a single rotation of the input shaft is inputted to the input shaft.

With such an apparatus for manufacturing the absorbent article, for each transport amount, an amount of rotation that is an integer multiple (an integer being greater than or equal to one) of the single rotation is inputted to the input shaft. Therefore, the reference signal can be readily set in such a manner that the first waveform appears at a portion of a specific transport amount in each unit transport amount. That is to say, the setting of the reference signal outputting section can be facilitated.

It is preferable that, in the apparatus for manufacturing an absorbent article as described above, for the unit transport amount, an amount of rotation that is an integer multiple an integer being greater than or equal to two) of a single rotation of the input shaft is inputted to the input shaft.

With such an apparatus for manufacturing the absorbent article, since the amount of rotation that is inputted to the input shaft for a unit transport amount becomes greater, the first waveform portion can be made to correspond precisely. As a result, an accuracy of a pass/fail determination of the actual processing position can be improved.

It is preferable that, in the apparatus for manufacturing an absorbent article as described above, the first waveform portion is set at a phase determined by internally dividing the one wavelength in a ratio of a distance from a border position of the semi-finished products neighboring in the transport direction to the allowable range of the process target position, to the unit transport amount.

With such an apparatus for manufacturing the absorbent article, the first waveform portion can be set to the reference signal securely and at a high accuracy by making it correspond to the allowable range of the process target position.

It is preferable that, in the apparatus for manufacturing an absorbent article as described above, at a predetermined point of time, a state in which the reference signal outputting section is outputting a signal having a phase corresponding to the process target position is made to correspond to a state in which the sensor section is detecting the same position as the process target position.

With such an apparatus for manufacturing the absorbent article, a pass/fail determination of the actual processing position can be performed positively.

A method of manufacturing an absorbent article, that, while a plurality of semi-finished products of the absorbent article is being transported in an aligned manner in a transport direction, processes the semi-finished product, and that inspects whether or not an actual processing position is within an allowable range of the process target position on the semi-finished product, includes:

detecting the actual processing position of the semi-finished product at a predetermined position in the transport direction and outputting a detection signal while the actual processing position of the semi-finished product is being detected;

outputting a reference signal having a waveform in which one wavelength is equivalent to a unit transport amount corresponding to a single semi-finished product, the reference signal having a first waveform portion at a phase corresponding to the allowable range in the wavelength; and determining whether or not the actual processing position is within the allowable range by comparing the detection signal with the reference signal.

With such a method of manufacturing the absorbent article, a pass/fail determination of the actual processing position can be performed by simply comparing the detection signal related to the actual processing position with the reference signal. Accordingly, the apparatus for manufacturing the absorbent article can be made at a low cost without using expensive inspection equipment such as an infrared camera and the investment burden can be reduced. As a result, the production cost of the absorbent article can be reduced.

Also, in addition to the reference signal, since the detection signal will also be outputted in accordance with the transport amount, an inspection can be performed at a high accuracy even if there is a change in the transport speed of the semi-finished product.

Present Embodiment

Absorbent Article 1

First, an absorbent article 1 manufactured by a manufacturing apparatus and a manufacturing method of the present embodiment will be described by taking a sanitary napkin 1 as an illustrative example. In the following explanation, regarding the sanitary napkin 1, a side which comes into contact with a human body is referred to as a front side and a side which comes into contact with underwear is referred to as a back side.

Figure 1B:
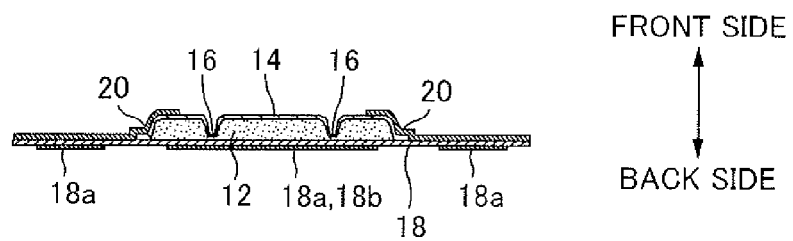
FIG. 1B is a sectional view of FIG. 1A taken along line B-B.

FIG. 1A is a plan view of the front side of the sanitary napkin 1. FIG. 1B is a sectional view of FIG. 1A taken along line B-B. As shown in FIG. 1A, the absorbent article 1 as a whole has an elongated shape extending in a predetermined direction. Hereinafter, this predetermined direction is referred to as a longitudinal direction and a direction orthogonal to this longitudinal direction is referred to as a width direction.

This absorbent article 1 includes, for example, an absorbent body 12 that absorbs liquid such as menstrual blood, a front sheet 14 that is provided so as to cover the front side of the absorbent body 12, a back sheet 18 that is provided to so as to cover the back side of the absorbent body 12 and a pair of side sheets 20, 20 that is provided along the longitudinal direction to cover both end portions in the width direction of the front sheet 14 so as to prevent leakage of liquid from both end portions in the width direction of the absorbent article 1.

The absorbent body 12 is a layered body in which liquid-absorbing fiber such as pulp fiber is layered in a substantially rectangular shape. Note that, here, for the sake of explanation, this layered body is not wrapped by a liquid permeable sheet such as tissue paper, but it may also be wrapped. Further, high-absorbent polymer may be mixed into the absorbent body 12.

The front sheet 14 is a liquid permeable sheet that has a substantially rectangular shape which is somewhat greater than a planar shape of the absorbent body 12 and a non-woven fabric such as air-through and spun-bond non-woven fabrics is used as its material. The constituent fiber of the non-woven fabric is, for example, a fiber of thermoplastic resin such as polyethylene and polyethylene terephthalate.

Note that, the absorbent body 12 and the front sheet 14 are joined by a hot-melt type adhesive agent in a state where they overlap with each other, and further, in this overlapped state, a groove embossing process is applied and a compression groove 16 is formed at a predetermined position by compression forming. With the compression groove 16, the absorbent body 12 and the front sheet 14 are further securely joined. Note that a pattern formed by the compression groove 16 is, for example, an annular pattern having a substantially rectangular shape that is elongated in the longitudinal direction as a whole. Further, when wearing the absorbent article 1, this compression groove 16 also serves as a bend-inducing portion so as to bend and fit along a wearer's body.

The back sheet 18 is a liquid permeable sheet of a material such as polyethylene or polypropylene and its planar shape is a substantially rectangular shape that is greater than the absorbent body 12 both in its longitudinal direction and its width direction. With the absorbent body 12 being placed on its front side, the back sheet 18 has, at least on both ends in the longitudinal direction, end seal portions 19a, 19b which are formed by being thermally deposited on the front sheet 14 by an end seal process and thus the absorbent body 12 is held between the back sheet 18 and the front sheet 14.

Note that, as shown in FIG. 1B, on a back side of the back sheet 18, an underwear-fixing adhesive 18a is applied, which fixes the absorbent article 1 on an inner side of the underwear when in use. Further, wing portions 18w, 18w protrude outwardly in the width direction at both ends in the width direction of the back sheet 18 and the underwear-fixing adhesive 18a is also applied on the back side of the wing portions 18w, 18w. When fixing the absorbent article 1 on underwear, these wing portions 18w, 18w are folded and fixed on an outer surface of the underwear by this underwear-fixing adhesive 18a. Note that the underwear-fixing adhesive 18a is applied at relevant portions of the absorbent article 1 by a separator tape (not shown) and is covered with the separator tape until use of the absorbent article 1.

<<<Manufacturing Apparatus and Manufacturing Method of Absorbent Article 1>>>

Figure 2:
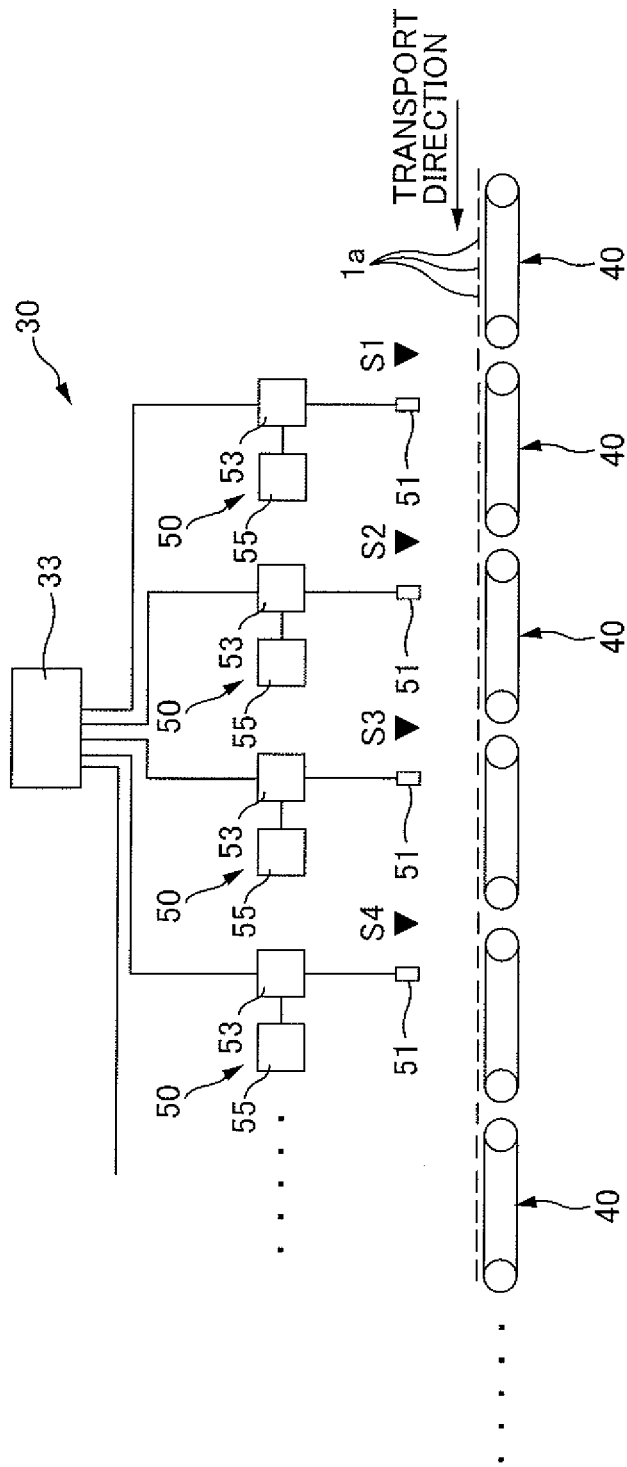
FIG. 2 is a schematic diagram of a production line 30 of the sanitary napkin 1.

FIG. 2 is a schematic diagram of a production line 30 of the absorbent article 1. The absorbent article 1 is manufactured in a production line 30. The production line 30 includes a transport mechanism 40 such as a conveyor. The conveyor 40 transports a semi-finished product 1a of the absorbent article 1, with its longitudinal direction being oriented in the transport direction, at a predetermined pitch in the transport direction. During the transportation, a processing device at each processing section S1, S2, . . . applies each type of processing on the semi-finished product 1a.

A sensor section 51 of an inspection device 50 is provided directly after each processing section S1, S2, . . . . Each inspection device 50 determines, regarding a process that was performed on the semi-finished product 1a by a processing section on its nearest upstream side, whether or not the actual processing position is out of an allowable range of a process target position. The determination result is sent to an overall control computer 33, and the overall control computer 33 makes a final determination based on all determination results sent from the respective inspection devices 50 and sorts the finished product of the absorbent article 1 into a non-defective product and a defective product. For example, in a case where any one of the determination results sent from the each inspecting devices 50 indicates a defective result, this finished product is discharged from the conveyor 40, at a discharge section (not shown) provided most downstream in the transport direction, in order to treat the finished product as a defective product.

In the description below, as illustrative examples of the processing section S1, S2, . . . , an explanation will be made with reference to an absorbent body forming section Sf that shapes the absorbent body 12 and places and joins it on the front sheet 14 and a groove embossing section Se that forms the compression groove 16 shown in FIG. 14 on the front sheet 14 on which the absorbent body 12 has been placed and joined. However, the basic concept of the inspection method of the present invention is basically common to all processing sections and thus can be applied to all processing sections related to the manufacturing of the absorbent article 1.

Figure 3:
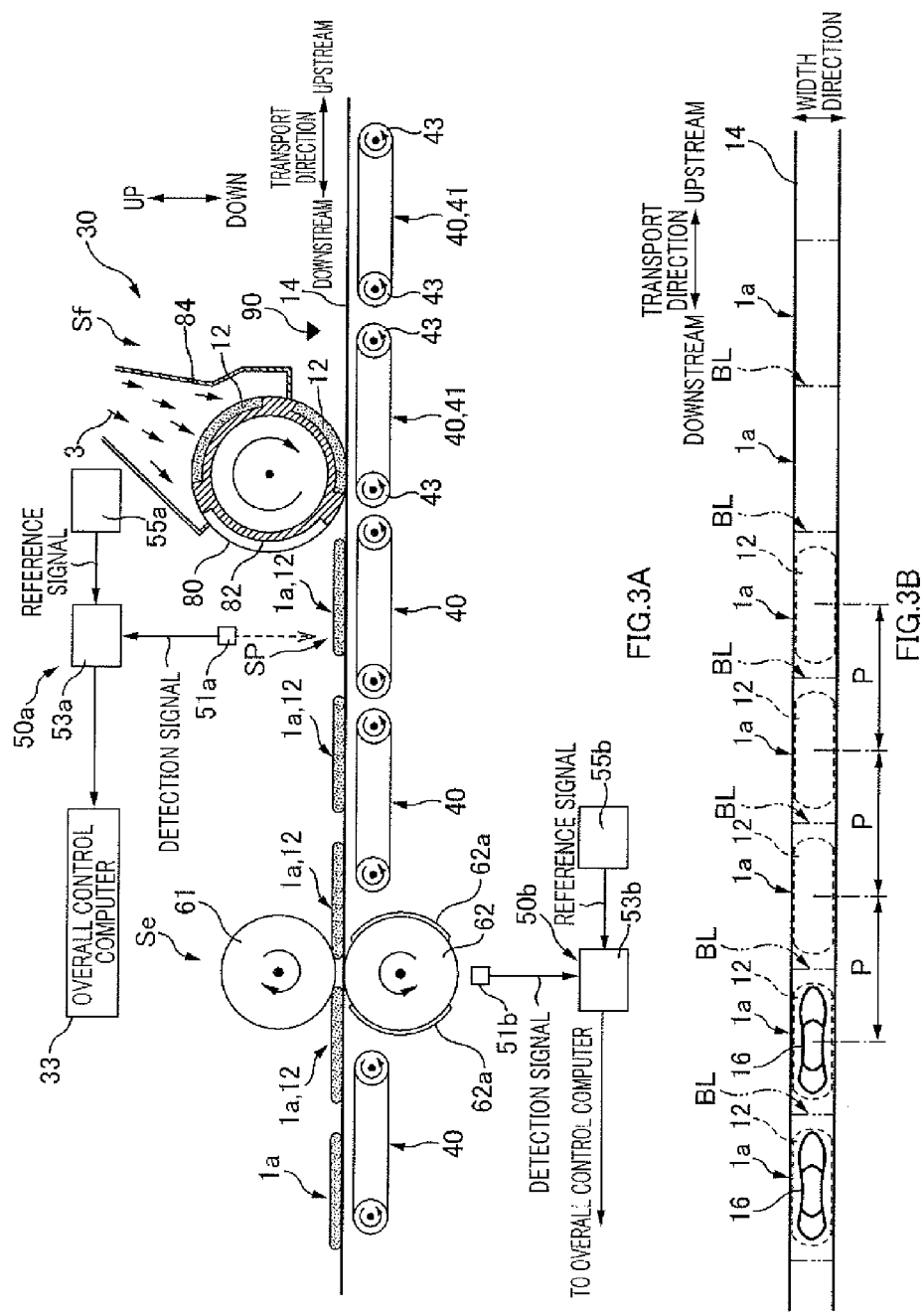
FIG. 3A is a side view of an absorbent body forming section Sf and a groove embossing section Se.
FIG. 3B is a schematic diagram viewed from the bottom (back side) illustrating a state in which the semi-finished product 1a has been processed at sections Sf and Se.

FIGS. 3A and 3B are explanatory diagrams of the absorbent body forming section Sf and the groove embossing section Se. FIG. 3A is a side view shown in a partially sectional view and FIG. 3B is a schematic diagram showing a state in which the semi-finished product 1a has been processed from the bottom (back side).

<<Absorbent Body Forming Section Sf>>

At the absorbent body forming section Sf, the formed absorbent body 12 is placed and joined to the front sheet 14 that corresponds to the semi-finished product 1a. Here, the front sheet 14 at a point of time of being transported to this absorbent body forming section Sf is in a state where it is not yet divided into individual products, in other words, in a state of a continuous sheet that continues in the transport direction. Then, while such front sheet 14 is being transported in a continuous manner in the transport direction by the conveyor 40, the absorbent body 12 that has been formed by a fiber stacking drum 80 driven and rotated in synchronous with the transport operation of the conveyor 40 is placed on and joined to the front sheet 14 at predetermined pitch P in the transport direction.

In the following, the semi-finished product 1a that is in a state where it is not yet divided in the transport direction is also referred to as a continuous body of the semi-finished product 1a. That is to say, the semi-finished product 1a is a single unit that may finally become a product and whose total length is the same value as the above-mentioned pitch P and, when these are connected together, they are referred to as a continuous body of the semi-finished products 1a. Note that, in FIG. 3B, a border between the semi-finished products 1a and 1a that are adjacent to each other in the transport direction is virtually indicated as a border position BL.

The conveyor 40 is a suction conveyor that transports, for example, the front sheet 14 by suction. That is to say, it has an endless belt 41 which is driven in a circulating manner and a large number of suction holes (not shown) are provided on an outer peripheral surface of the endless belt 41. Then, with air suction through the suction hole, the front sheet 14, as a continuous body of the semi-finished product 1a, is held by suction on the peripheral surface of the endless belt 41 and is transported. The endless belt 41 is driven in a circulating manner by a plurality of drive rollers 43 that is disposed in an aligned manner in the transport direction. The drive roller 43 is driven by using, for example, an electric motor as a drive source. An amount of transport of the continuous body of the semi-finished product 1a can be derived by, for example, measuring an amount of rotation of the drive roller 43 by a rotation amount measuring instrument such as a rotary encoder and multiplying the measured amount of rotation (angle of rotation (°)) by a length of arc of the drive roller 43 corresponding to a center angle of one degree (1°). Further, a transport speed (m/min) can be derived by differentiating the derived transport amount by an appropriate differentiator or the like.

The fiber stacking drum 80 is a substantially cylindrical body that is driven and rotated. On its outer peripheral surface, in the circumferential direction, a shaping mold 82 having a recessed shape is formed at the above-mentioned pitch P. A duct 84 is disposed at a predetermined position in the circumferential direction and a mix-in air 3 containing pulp fiber is supplied through the duct 84 toward the outer peripheral surface. Accordingly, when the shaping mold 82 passes the position of the duct 84 by the driven and rotated fiber stacking drum 80, pulp fiber is stacked in the shaping mold 82. Thereafter, when passing the position of the conveyor 40, the pulp fiber is demolded from the shaping mold 82 by a suction force of the conveyor 40 and the absorbent body 12 is placed on the front sheet 14 on the conveyor 40.

The fiber stacking drum 80 is driven and rotated in synchronous with the transport operation of the conveyor 40. That is to say, the circumferential speed (m/min) of the fiber stacking drum 80 is speed-controlled so as to become substantially the same speed as the transport speed (m/min) of the conveyor 40.

Therefore, for example, at the beginning of operation of the production line 30, the fiber stacking drum 80 may be positioned by making a relative rotation against the front sheet 14, which is a continuous body of the semi-finished product 1a, in such a manner that the shaping mold 82 comes into contact with the placing target position (corresponds to the process target position) of the absorbent body 12 on the front sheet 14. Then, after such positioning, basically, as long as the circumferential speed of the fiber stacking drum 80 and the transport speed of the conveyor 40 do not become greatly different, the absorbent body 12 will be placed and joined on the continuous body of the semi-finished product 1a within an allowable range of the placing target position of the absorbent body 12 on the semi-finished product 1a.

It is to be noted that in a case where the circumferential speed of the fiber stacking drum 80 and the transport speed of the conveyor 40 has become significantly different due to, for example, poor speed control, the actual placing position (corresponding to the actual processing position) of the absorbent body 12 may become out of the allowable range of the placing target position.

Therefore, an inspecting device 50a dedicated to the absorbent body forming section Sf is provided, and the inspecting device 50a determines whether or not the actual placing position of the absorbent body 12 is within the allowable range of the placing target position.

Also, as shown in FIG. 3A, an adhesive applying device 90 is provided upstream of the fiber stacking drum 80, and with this adhesive applying device 90, a hot-melt adhesive is applied in advance at the above-mentioned pitch P in the transport direction at a placing target portion of the front sheet 14 that is a continuous body of the semi-finished product 1a.

The inspecting device 50a includes a sensor section 51a that detects the actual placing position of the absorbent body 12, a determining section 53a that performs a pass/fail determination of the actual placing position based on the detection signal of the sensor section 51a and a reference signal outputting section 55a that outputs a reference signal which is used as a comparison that is compared with a detection signal from the sensor section 51a when the determining section 53a performs the above-mentioned pass/fail determination.

Figure 4:
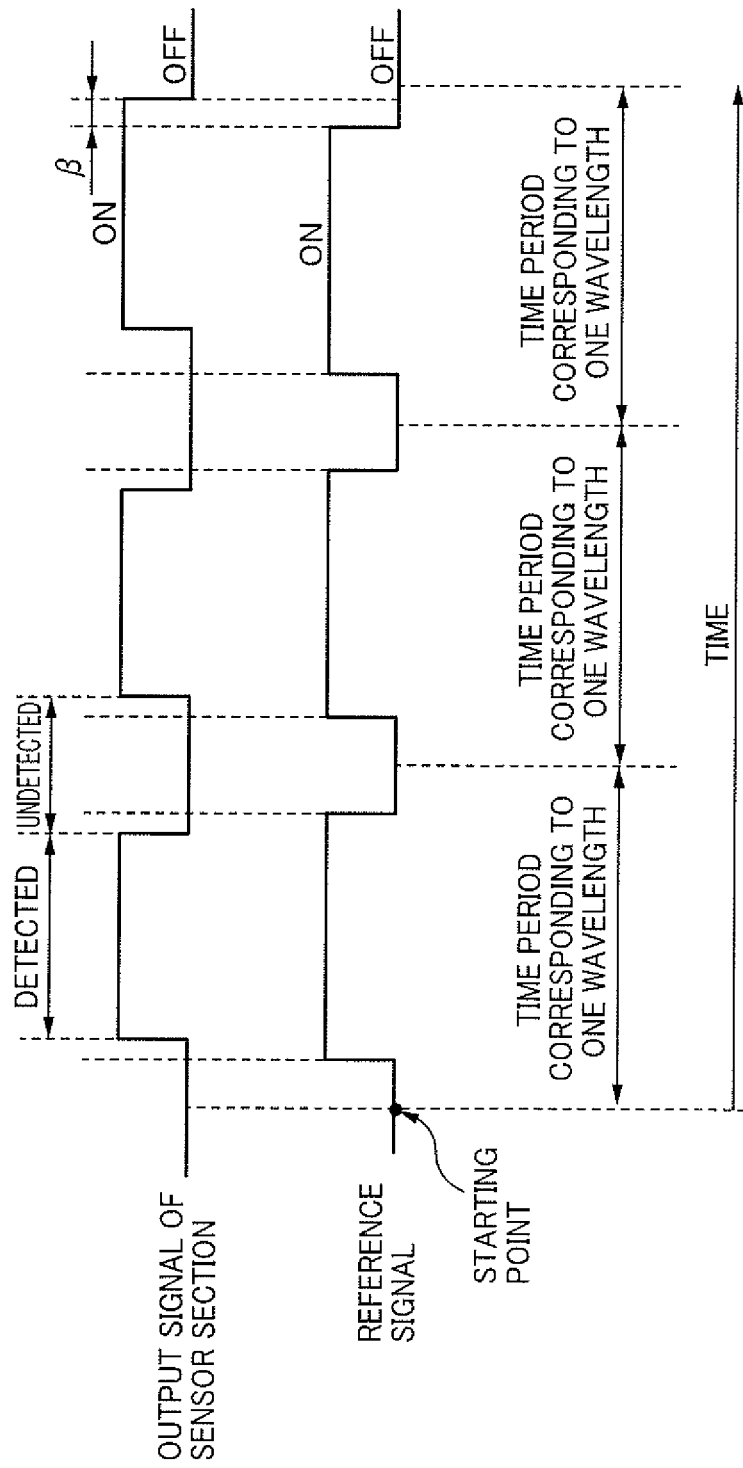
FIG. 4 is an explanatory diagram of an output signal of a sensor section 51a and a reference signal regarding an inspecting device 50a for the absorbent body forming section Sf.

The sensor section 51a is provided at a position downstream of the fiber stacking drum 80 in the transport direction (corresponds to the predetermined position). Then, it detects the actual placing position of the absorbent body 12 every time the absorbent body 12 passes below the position at which the sensor section 51a is provided, and outputs the output signal while detecting. FIG. 4 illustrates an output signal of the sensor section 51a, and in this example, a rectangular pulse is outputted as the detection signal only when the absorbent body 12 is being detected, and it shows a non-output state when not being detected. The horizontal axis represents time. A photoelectric tube that outputs an electric signal corresponding to an amount of received light intensity is one of illustrative examples of such sensor section 51a.

The determining section 53a may be a computer having a processor that executes an appropriate calculation program, a sequencer and the like. As shown in FIG. 3A, by comparing the detection signal sent from the sensor section 51a with the reference signal transmitted from the reference signal outputting section 55a, the determining section 53a determines whether or not the actual placing position of the absorbent body 12 is within the allowable range of the placing target position. A program for performing this determination is prestored in a memory and the like of the determining section 53a.

Figure 5:
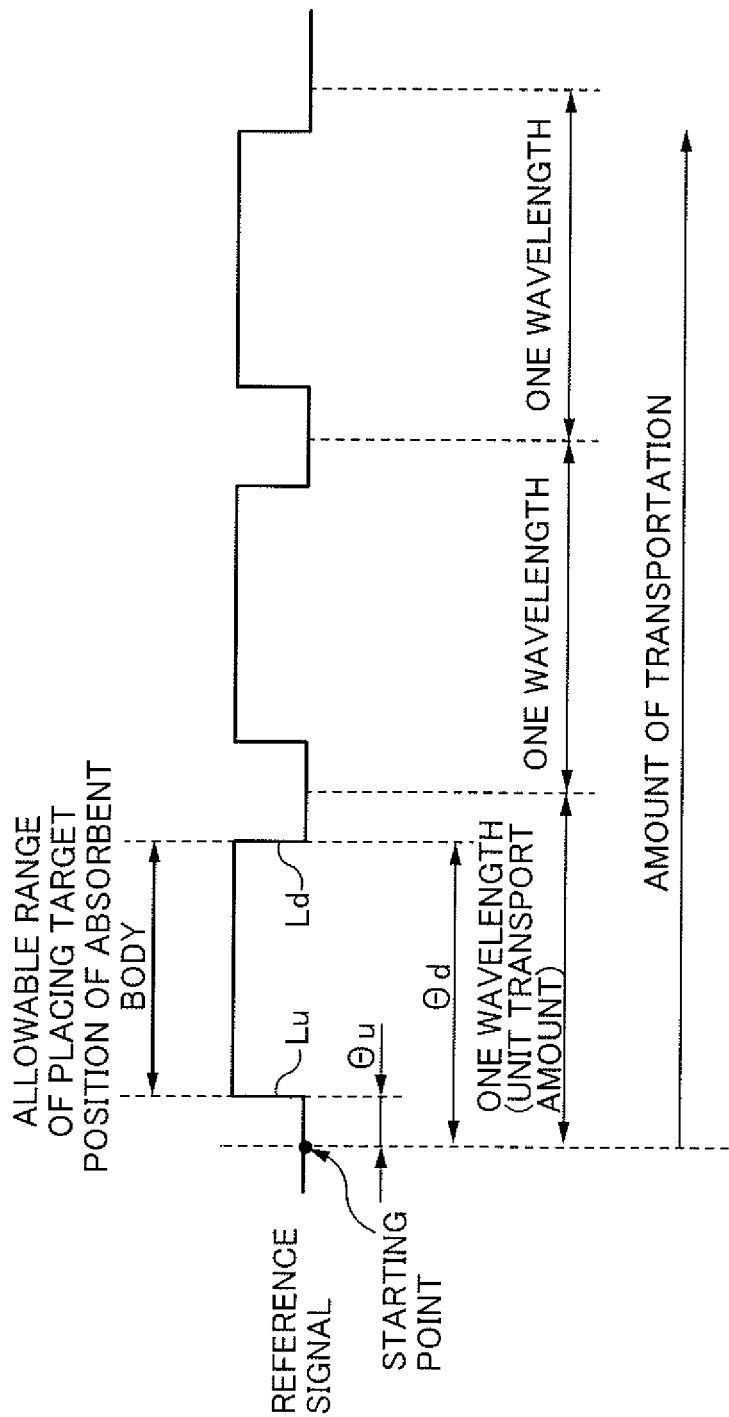
FIG. 5 is an explanatory diagram illustrating a reference signal.

Here, the reference signal is, as shown in FIG. 5, a signal in which the allowable range of the placing target position is indicated in connection with the transport amount. In other words, it is a signal that is outputted in synchronous with the transport amount and has a waveform with its one wavelength being equal to the transport amount corresponding to a single semi-finished product (the same value as the above-mentioned pitch P and hereinafter also referred to as a "unit transport amount"). This signal further includes a rectangular pulse (corresponds to the first waveform portion) at a phase corresponding to the allowable range of the placing target position of the absorbent body 12.

It is to be noted that the horizontal axis in FIG. 5 represents the transport amount, whereas the horizontal axis when comparing with the detection signal shown in FIG. 4 is the time axis. That is to say, in relation to the transport amount, the reference signal outputting section 55a outputs the reference signal while maintaining the relationship shown in FIG. 5 and thus, in relation to the time axis, it outputs a value of the reference signal corresponding to the transport amount at relevant time. On the other hand, basically, the output signal of the sensor section 51a also shows the state of detection at relevant time, but such state of detection changes in accordance with the transport amount.

Therefore, for example, at an appropriate timing such as before operating the production line 30, once having made the state at which the reference signal outputting section 55a is outputting a signal of a phase corresponding to the placing target position of the absorbent body 12 to correspond to the state at which the sensor section 51a is detecting the above-mentioned placing target position, thereafter, the pass/fail determination of the actual placing position can be performed by simply comparing both the reference signal and the output signal of the sensor section 51a using the same time as a key.

Explaining by way of specific example, first, before start operating the production line 30, as an initial setting, the front sheet 19, which is a continuous body of the semi-finished product 1a, is moved in the transport direction so as to position the placing target position at a position where the sensor section 51a is provided, i.e., a detection objective position SP of the sensor section 51a on the conveyor 40 (see FIG. 3A). In this state, the reference signal outputting section 55a is operated to set the phase of the reference signal to a phase corresponding to the placing target position.

Thereafter, the operation of the production line 30 is started and the front sheet 14 which is a continuous body of the semi-finished product 1a is transported by the conveyor 40. At this time, the phase of the reference signal and the output state of the output signal of the sensor section 51a that are outputted at the same time should be both indicating the state of the same phase of the semi-finished product 1a.

Accordingly, thereafter, the determining section 53a performs an inspection by simply comparing the reference signal and the output signal of the sensor section 51a as described below. That is to say, when comparing the reference signal and the output signal of the sensor section 51a at the same time, as can be seen from the waveform at the right hand side end in FIG. 4, in a case where the output signal of the sensor section 51a is in an ON state (output state of the detection signal) even if the reference signal is in an OFF state (in a dropped state), the determining section 53a determines that the semi-finished product 1a has failed since its actual placing position is out of the allowable range. On the other hand, in other cases they are determined as passed goods.

Figure 6:
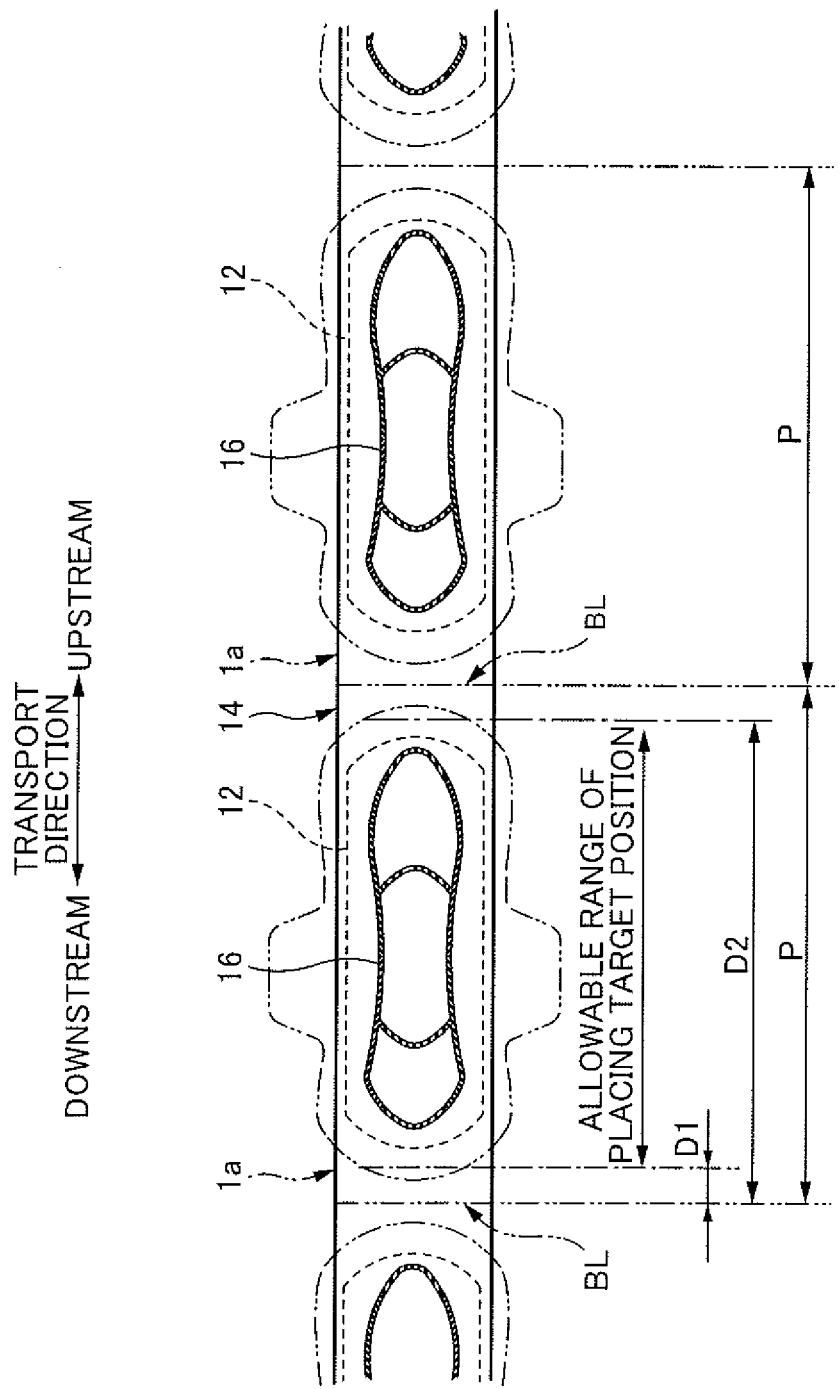
FIG. 6 is an explanatory diagram illustrating a calculation method of phases θu-θd at which rectangular pulses should be set in the reference signal.

Such a reference signal is generated at the reference signal outputting section 55a. It has been described above that the waveform of this reference signal has a rectangular pulse indicating the allowable range of the placing target position of the absorbent body 12. The above-mentioned phase $\theta u$-$\theta d$ at which the rectangular pulse is to be set (see FIG. 5) is determined as described below. FIG. 6 is a explanatory diagram thereof. Note that, in FIG. 6, the contour of the finished good is virtually indicated by a dash-double-dot line so as to correspond to the semi-finished product 1a.

As shown in FIG. 6, when, for example, the starting point of the waveform of the reference signal is made to correspond to the border position BL between the semi-finished products 1a and 1a, which are adjacent to each other in the transport direction, the phase $\theta u$ of a leading edge line Lu of the rectangular pulse in FIG. 5 can be derived by dividing a design value D1 of a distance between the above-mentioned border position BL and the downstream limit of the allowable range of the placing target position by the above-mentioned unit transport amount. Further, the phase $\theta d$ of a trailing edge line Ld of the rectangular pulse can be derived by dividing a design value D2 of a distance between the above-mentioned border position BL and an upstream line of the allowable range of the placing target position by the above-mentioned unit transport amount.

It is to be noted that the unit transport amount is, for example, obtained as a distance between the border positions BL and BL that are located at both ends of the semi-finished product 1a and thus is the same value as the above-mentioned pitch P.

Figure 7:
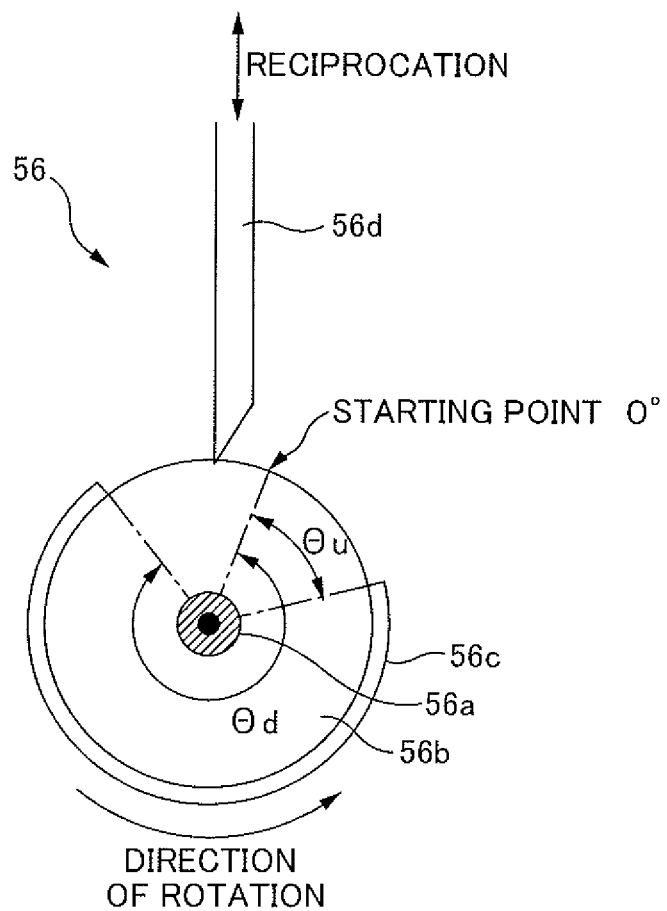
FIG. 7 is an explanatory diagram illustrating a mechanical cam switch 56.

For example, a cam switch can applied to this reference signal outputting section 55a. The cam switch may be broadly grouped into a mechanical cam switch and an electronic cam switch. As shown in FIG. 7, the mechanical cam switch 56 includes a plate cam 56b of substantially a precise circled shape that integrally rotates with an input shaft 56a, and on an outer peripheral surface of the plate cam 56b, protruded portions 56c are formed as a cam curve for a predetermined range of rotation angle $\theta u$-$\theta d$ starting at a starting point that is a predetermined reference position (for example, a rotational angle $\theta°$). It is to be noted that, the above-mentioned range of rotation angle $\theta u$-$\theta d$ where the protruded portions 56c are formed is the same value as the phase $\theta u$-$\theta d$ derived as the above-mentioned allowable range. Further, a cam follower 56d is provided so as to oppose the outer peripheral surface of the plate cam 56b and the cam follower 56d is guided so as to be relatively movable in the radial direction of the plate cam 56b while maintaining a state in which the cam follower 56d is in contact with the outer peripheral surface of the plate cam 56b. Accordingly, the cam follower 56d performs a reciprocating movement by being pushed by the protruded portion 56c in accordance with the rotation of the plate cam 56b inputted from the input shaft 56a. By inputting this reciprocating movement operation to an appropriate switch circuit, the reference signal having the above-mentioned rectangular pulse is generated.

Here, in order that an amount of rotation corresponding to a single rotation will be inputted into the input shaft 56a for a unit transport amount of the semi-finished product 1a, the above-mentioned input shaft 56a is connected to the drive roller 43 of the conveyor 40 via a mechanism that converts a number of rotations (not shown) such as an appropriate decelerator (e.g., gear train). Therefore, the reference signal is set in such a manner that the above-mentioned rectangular pulse repeatedly appears at a specific portion of the transport amount in each unit transport amount. That is to say, it is set in such a manner that the rectangular pulse is appears at phase $\theta u$-$\theta d$ of each waveform of the reference signal shown in FIG. 5.

It is to be noted that this reference signal outputting section 55a may be constituted by an electronic cam switch. Also in this case, it has the input shaft 56a and generates the rectangular pulse based on the rotation of the input shaft 56a. However, unlike the mechanical cam switch 56, since the rectangular pulse is configured in such a manner that it can be electrically set at any rotational angle range $\theta u$-$\theta d$ of the input shaft 56a, the freedom in setting the phase of the rectangular pulse is higher than the mechanical cam switch. An illustrative example of such an electronic cam switch is VARICAM (product name, manufactured by NSD Corporation).

For this electronic cam switch, in stead of inputting the rotation into the input shaft 56, an output signal of a rotary encoder of the drive roller 43 or the conveyor 40 may be directly inputted. In such a case, the electronic cam switch recognizes the above-mentioned unit transport amount by counting the number of pulses of the output signal from the rotary encoder. That is to say, a value of the number of pulses corresponding to the unit transport amount is preset in the electronic cam switch and thus the unit transport amount and the above-mentioned phases, etc. are recognized.

The inspecting device 50a for the absorbent body forming section Sf has been described above. With such inspecting device 50a, the pass/fail determination of the actual placing position (corresponds to actual processing position) of the absorbent body 12 can be performed with a simple constitution including the sensor section 51a, the determining section 53a and the reference signal outputting section 55a. Therefore, the apparatus for manufacturing the absorbent article 1 can be made at a low cost without using expensive inspection equipment such as an infrared camera and the investment burden can be reduced. As a result, the production cost of the absorbent article 1 can be reduced. It is to be noted that, as has been described above, the pass/fail determination result for each semi-finished product 1a by the determining section 53a is transmitted to the overall control computer 33.

<<Groove Embossing Section Se>>

At the groove embossing section Se, by processing and forming the compression groove 16 shown in FIG. 1A on the front sheet 14 to which the above-mentioned absorbent body 12 is placed and joined, the front sheet 14 and the absorbent body 12 are further strongly joined and integrated. That is to say, the continuous body of the semi-finished product 1a at the time of being transported to the groove embossing section Se is in a state where the absorbent bodies 12 are intermissively placed at the predetermined pitch P in the transport direction on the continuous body of the front sheet 14 that continues in the transport direction. Then, while such continuous body of the semi-finished product 1a is being continuously transported in the transport direction by the conveyor 40, the continuous body of the semi-finished product 1a is passed through a roll gap between a pair of upper and lower embossing rolls 61 and 62 (corresponds to the processing device) that is driven and rotated in synchronous with the transport operation of the conveyor 40. Accordingly, the compression groove 16 is compressed and formed for each semi-finished product 1a.

The structure of the conveyor 40 is the same as above.

The upper roll 61 of the embossing rolls is a roll having a smooth outer peripheral surface, whereas, the lower roll 62 is a roll having embossing ribs 62a and 62a corresponding to the above-mentioned compression grooves 16 which are formed in a protruded manner on its outer peripheral surface. The embossing rib 62a is provided in such a manner that two of which are provided so as to align in the circumferential direction of the lower roll 62 and thus the compression grooves 16 for two semi-finished products can be formed with a single rotation of the lower roll 62. That is to say, a circumferential length of the lower roll 62 is set at double the length of the unit transport amount and each embossing rib 62a, 62a is provided so as to bisect the circumferential length. Further, the upper roll 61 and the lower roll 62 are driven and rotated in synchronous with the transport operation of the conveyor 40. That is to say, the circumferential speed (m/min) of the upper roll 61 and the lower roll 62 is controlled so as to become substantially the same speed as the transport speed (m/min) of the conveyor 40.

Therefore, for example, at the beginning of operation of the production line 30, the lower roll 62 may be positioned by making a relative rotation against the continuous body of the semi-finished product 1a, in such a manner that the embossing rib 62a comes into contact with the process target position of the compression groove 16 on a single semi-finished product 1a. Then, after such positioning, basically, as long as the circumferential speed of the embossing rolls 61 and 62 does not become significantly different from the transport speed of the conveyor 40, the compression groove 16 will be formed on the continuous body of the semi-finished product 1a within the allowable range of the process target position of the compression groove 16 on semi-finished product 1a.

It is to be noted that in a case where the circumferential speed of the embossing rolls 61 and 62 and the transport speed of the conveyor 40 becomes significantly different due to a poor speed control, the processing position of the actual compression groove 16 may become out of the allowable range of the process target position.

Therefore, an inspecting device 50b dedicated to the groove embossing section Se is provided and the inspecting device 50b determines whether or not the actual processing position of the compression groove 16 is within the allowable range of the processing target position.

The inspecting device 50b includes a sensor section 51b that detects the actual processing position of the compression groove 16, a determining section 53b that performs a pass/fail determination of the actual processing position based on the detection signal of the sensor section 51b and a reference signal outputting section 55b that outputs a reference signal which is used as a comparison with the detection signal from the sensor section 51b when the determining section 53b performs the above-mentioned pass/fail determination.

Figure 8:
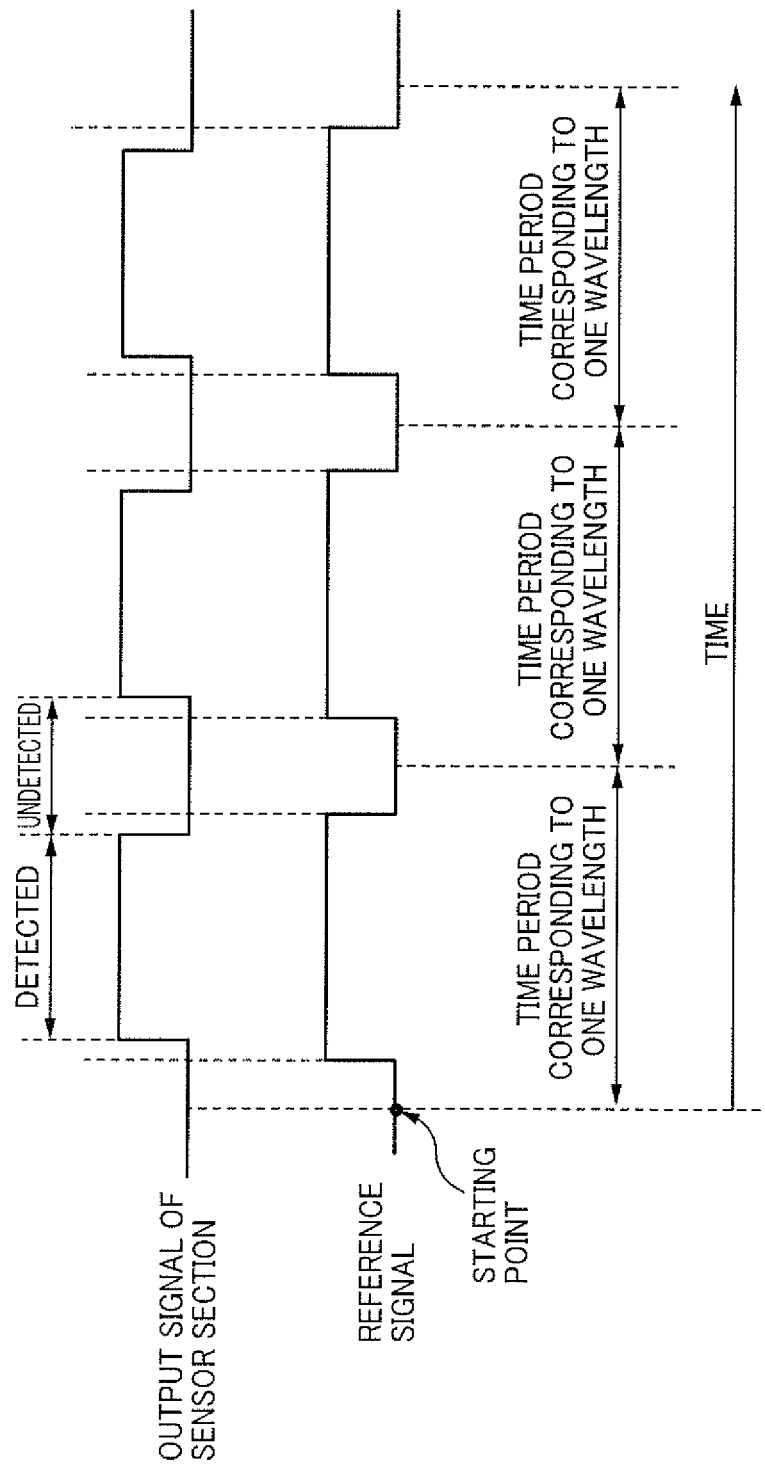
FIG. 8 is an explanatory diagram of an output signal of a sensor section 51b and a reference signal regarding an inspecting device 50b for the groove embossing section Se.

The sensor section 51b is, for example, as shown in FIG. 3A, a proximity switch that is provided in the vicinity of a predetermined position in the circumferential direction of the lower roll 62 of the embossing rolls and, every time the embossing rib 62a and 62b passes near the sensor section 51b in accordance with the rotation of the lower roll 62, detects it as an actual processing position of the compression groove 16 and outputs the detection signal while detecting. That is to say, the actual processing position of the compression groove 16 on the semi-finished product 1a is indirectly detected via the detection of the embossing rib 62a. FIG. 8 illustrates the output signal of the sensor section 51b. In this example, a rectangular pulse is outputted only while detecting the embossing rib 62a and it becomes a non-output state while not detecting. Note that the horizontal axis represents time.

The structure of the reference signal outputting section 55b is substantially the same as above and it is, for example, a cam switch.

The structure of the determining section 53b is also substantially the same as above. That is to say, by comparing the detection signal sent from the sensor section 51a with the reference signal transmitted from the reference signal outputting section 55b, the determining section 53b determines whether or not the actual processing position of the compression groove 16 is within the allowable range of the process target position. The reference signal is, for example, as shown in FIG. 5, outputted while being synchronized with the transport amount. Then, it has a waveform of the above-mentioned transport amount as a one wavelength and, for each waveform, a rectangular pulse (corresponds to the first waveform portion) is provided at a phase corresponding to the allowable range of the process target position of the compression groove 16.

Therefore, in a manner similar to the case of the above-mentioned absorbent body forming section Sf, for example, at an appropriate timing such as at the beginning of operation of the production line 30, once making the state in which the reference signal outputting section 55b is outputting a signal of the phase corresponding to the process target position of the compression groove 16 to correspond to the state in which the sensor section 51b is detecting the above-mentioned process target position, thereafter, a pass/fail determination of the actual processing position can be performed by simply comparing the reference signal and the output signal of the sensor section 51b using the same time as the key.

Other Embodiments

Embodiments of the present invention have been discussed above, however, the present invention is not limited to such embodiments and variants described below may also be provided.

In the embodiments described above, the manufacturing apparatus and manufacturing method of the sanitary napkin 1 that absorbs excreted liquid such as menstrual blood have been described. However, the scope of the present invention is not limited thereto and the present invention may, for example, be applied to manufacturing of disposable diapers that absorb excreted liquid such as urine, a pet sheet that absorbs excreted liquid of pets, etc.

In the embodiments described above, the absorbent body forming section Sf and the groove embossing section Se have been described as an example of the processing section. However, as long as it is a processing section related to the manufacturing of the absorbent article 1, it is by no means limited thereto and the present invention may be applied to other processing sections.

For example, the present invention may be applied to a section that applies adhesive for attaching to underwear 18a to the back sheet 18 of the continuous body of the semi-finished product 1a, to a section that covers this adhesive for attaching to underwear 18a with a single sheet-type protection sheet, and further to a section that punches out the continuous body of the continuous body of the semi-finished product 1a into a shape of a finished good. In other words, in addition to a process of deforming the semi-finished product 1a by, for example, exerting an external force on the semi-finished product 1a, the concept of "processing" described above includes a process of applying the adhesive on the semi-finished product 1a and joining other members, a process of dividing the continuous body of the semi-finished product 1a into units of product.

In the embodiments described above, the photoelectric tube and the proximity switch have been taken as illustrative examples of the sensor sections 51a and 51b. However, as long as the actual processing position can be directly or indirectly detected, it is by no means limited thereto and may be other sensors depending on the type of processing, such as, for example, a pressure switch that outputs a detection signal having an intensity that depends on an acting pressure.

In the embodiments described above, the cam switch has been taken as an example of the reference signal outputting section 55a and 55b. However, as long as it can output a reference signal having a waveform with a wavelength equivalent to a unit transport amount corresponding to a semi-finished product 1a and having a first waveform portion at a phase corresponding to the allowable range of a process target position in the wavelength, it is by no means limited to the cam switch.

In the embodiments described above, the conveyor 40 has been illustrated as the transport mechanism. However, it is by no means limited thereto. It may be a transport mechanism in which a plurality of transport rollers aligns in the transport direction and the continuous body of the semi-finished product 1a is transported by being directly in contact with these transport rollers.

In the embodiments described above, the case in which the processing is performed on the continuous body of the semi-finished product 1a has been illustratively described. However, the semi-finished product 1a need not be a continuous body. For example, the present invention may be applied to a processing section that applies a certain process while the absorbent article 1 that serves as the semi-finished product 1a is separately transported at a predetermined pitch in the transport direction.

In the embodiments described above, the rectangular pulse related to the waveform of the reference signal and the detection signal has been illustratively described. However, it is by no means limited thereto and may be, for example, a trapezoidal pulse or a triangular pulse.

In the embodiments described above, the input shaft 56a of the cam switch 56 has been set in such a manner that an amount of rotation corresponding to a single rotation is inputted for a unit transport amount of the semi-finished product 1a. However, it is by no means limited thereto. For example, the amount of rotation inputted to the input shaft 56a may be set to an amount of rotation that is an integer multiple (a multiple of greater than or equal to one) of the above-mentioned single rotation per unit transport amount. Also in this case, it can be set in such a manner that the above-mentioned rectangular pulse repeatedly appears at a specific portion of the transport amount for each unit transport amount. It is to be noted that, in a case where an integer value of greater than or equal to two is set as the above-mentioned integer multiple, an amount of rotation that is inputted to the input shaft 56a per unit transport amount will be greater. Thus, it can be more precisely matched with the target phase of the rectangular pulse and thus an accuracy of pass/fail determination of the actual processing position can be improved. That is to say, higher resolution can be obtained.

In the embodiments described above, the peripheral length of the lower roll 62 of the emboss rolls has been set to double the length of the unit transport amount (a transport amount corresponding to a single semi-finished product). However, as long as it is set to an integer multiple of the unit transport amount (a multiple of greater than or equal to one), it is by no means limited thereto.

In the embodiments described above, the determining section 53 is provided for each processing section. However, it is by no means limited thereto. For example, a single determining section 53 may be shared between some or all of the processing sections. In this case, the sensor section 51 and the reference signal outputting section 55 of the respective corresponding sections sends the detection signal and the reference signal respectively to the determining section 53. Then, based on such detection signal and the reference signal, the pass/fail determination is made for each processing section.

In the embodiments described above, a portion that may become a main body of the absorbent article 1 has been illustratively described as the semi-finished product 1a. However, the concept of the semi-finished product 1a is not limited to the portion that may become the main body and may, for example, include a concept of a component that is to be assembled with the main body. Hereinafter, a separator tape will be illustratively described as an example of the semi-finished product 1a.

The separator tape is, for example, produced at a separator tape processing section that is provided in parallel with the production line 30 of the above-mentioned absorbent article 1.

To this separator tape processing section, a separator tape that serves as the semi-finished product 1a is supplied as a continuous body that continues in the transport direction. Then, at this processing section, first, an adhesive is applied at a predetermined pitch to the continuous body of the separator tape. This adhesive is, for example, the adhesive for attaching to underwear 18b as shown in FIG. 1B. Then, the separator tape is wound on a cutter roll and transported, and, at the end of this transport, cut at a predetermined pitch in the transport direction by an external peripheral blade of the cutter roll. Thus, a separator tape in a single sheet form is produced. Thereafter, a single sheet-like separator tape merges with the production line 30 of the main body of the absorbent article 1 and is attached to the main body of the absorbent article 1.

Here, the adhesive is basically applied to the separator tape that has been cut into a single sheet at portions corresponding to an upstream end and a downstream end in the transport direction. However, there may be a case in which the actual applying position is offset from the allowable range of the applying target position. In such a case, the adhesive will be applied from the upstream end to the downstream end, which may cause troubles such as easily sticking onto objects around it.

Accordingly, an inspecting device for the separator tape processing section is provided.

In a similar manner to the above, the inspecting device includes a sensor section, a reference signal outputting section and a determining section.

The sensor section is provided at a predetermined position in the transport direction of the separator tape, detects the actual applying position every time the actual applying position passes by and outputs a detection signal while detecting.

On the other hand, the input shaft of the cam switch related to the reference signal outputting section is, via an appropriate device that converts a number of rotations, connected to a drive rotation axis that drives and rotates the cutter roll. Thereby, the reference signal outputting section outputs a reference signal. Here, the cutter roll also serves as a transport mechanism of the continuous body of the separator tape. Accordingly, the reference signal may output a waveform having one wavelength of the unit transport amount that corresponds to a single sheet separator sheet, and further, for each waveform, a rectangular pulse is provided at a phase corresponding to the allowable range of the application target position of the adhesive. Therefore, the determining section can determine whether or not the actual applying position of the adhesive is in an allowable range of the application target position by comparing the reference signal with the detection signal of the sensor section.

In a similar manner to the above, the waveform of the reference signal includes a single rectangular pulse per one wavelength for a unit transport amount corresponding to a single semi-finished product 1a. However, the number of pulses is by no means limited thereto, and a plurality of rectangular pulses may be set in one wavelength.

In detail, in a processing section in the production line of an open-type disposable diaper (a type of diaper in which the abdominal side and the dorsal side are attached by a fastening tape member when worn by the wearer), a pair of fastening tape member is attached in the transport direction onto the semi-finished product 1a of each diaper that is transported continuously in a transversal flow (the width direction of the diaper aligns with the transport direction and a plurality of diapers are aligned at a predetermined pitch in the transport direction). When inspecting the actual attaching position for each fastening tape member, as a waveform of a reference signal, a wave form having a rectangular pulse may be set at each of the two phases corresponding to the target attaching position of the fastening tape member in a single waveform Thereby, an inspection of a case in which a single semi-finished product has two parts of the same kind can be performed.

LIST OF REFERENCE NUMERALS 1 sanitary napkin (absorbent article), 1a semi-finished product,
3 mix-in air, 12 absorbent body, 14 front sheet, 16 compressed groove,
18 back sheet, 18a adhesive for attaching to underwear,
18b adhesive for attaching to underwear,
18w wing portion, 19a end seal portion, 19b end seal portion,
20 side sheet, 30 production line, 33 overall control computer,
40 conveyor (transport mechanism), 41 endless belt, 43 drive roller,
50 inspecting device, 50a inspecting device, 50b inspecting device,
51 sensor section, 51a sensor section, 51b sensor section,
53 determining section, 53a determining section, 53b determining section,
55 reference signal outputting section, 55a reference signal outputting section,
55b reference signal outputting section,
56 mechanical cam switch, 56a input shaft, 56b plate cam, 56c protruded portion,
56d follower, 61 upper roll of embossing rolls (processing device),
62 lower roll of embossing rolls (processing device), 62a embossing rib, 80 fiber stacking drum, 82 shaping mold, 84 duct,
90 adhesive applying device,
BL border position, Ld leading edge line, Lu trailing edge line,
Sf absorbent body forming section, Se groove embossing section,

The invention claimed is:

1. An apparatus for manufacturing an absorbent article, comprising:
   a processing device that, while a plurality of semi-finished products of the absorbent article is being transported in an aligned manner in a transport direction, processes the semi-finished product; and
   an inspecting device that, while the plurality of semi-finished products of the absorbent article is being transported in the aligned manner in the transport direction, inspects whether or not an actual processing position by the processing device is within an allowable range of the process target position on the semi-finished product,
   wherein, the inspecting device includes,
   a sensor section that is located at a predetermined position in the transport direction and that outputs a detection signal while the actual processing position of the semi-finished product is being detected,
   a reference signal outputting section that outputs a reference signal having a waveform in which one wavelength is equivalent to a unit transport amount corresponding to a single semi-finished product, the reference signal having a first waveform portion at a phase corresponding to the allowable range in the wavelength, and
   a determining section that determines whether or not the actual processing position is within the allowable range by comparing the detection signal with the reference signal.

2. An apparatus for manufacturing an absorbent article according to claim 1, wherein,
   a transport operation of the plurality of semi-finished products in the transport direction is performed by a transport mechanism;
   the reference signal outputting section has an input shaft to which a rotational operation synchronized with the transport operation of the transport mechanism is inputted, the reference signal outputting section being capable of setting the first waveform portion to correspond to a predetermined phase of an angle of rotation of the input shaft; and
   for the unit transport amount, an amount of rotation that is an integer multiple (an integer being greater than or equal to one) of a single rotation of the input shaft is inputted to the input shaft.

3. An apparatus for manufacturing an absorbent article according to claim 2, wherein,
   for the unit transport amount, an amount of rotation that is an integer multiple (an integer being greater than or equal to two) of a single rotation of the input shaft is inputted to the input shaft.

4. An apparatus for manufacturing an absorbent article according to claim 1, wherein, the first waveform portion is set at a phase determined by internally dividing the one wavelength in a ratio of a distance from a border position of the semi-finished products neighboring in the transport direction to the allowable range of the process target position, to the unit transport amount.

5. An apparatus for manufacturing an absorbent article according to claim 4, wherein, at a predetermined point of time, a state in which the reference signal outputting section is outputting a signal having a phase corresponding to the process target position is made to correspond to a state in which the sensor section is detecting the same position as the process target position.

6. A method of manufacturing an absorbent article, that, while a plurality of semi-finished products of the absorbent article is being transported in an aligned manner in a transport direction, processes the semi-finished product, and that inspects whether or not an actual processing position is within an allowable range of the process target position on the semi-finished product, comprising:
   detecting the actual processing position of the semi-finished product at a predetermined position in the transport direction and outputting a detection signal while the actual processing position of the semi-finished product is being detected;
   outputting a reference signal having a waveform in which one wavelength is equivalent to a unit transport amount corresponding to a single semi-finished product, the reference signal having a first waveform portion at a phase corresponding to the allowable range in the wavelength; and
   determining whether or not the actual processing position is within the allowable range by comparing the detection signal with the reference signal.

* * * * *